(12) United States Patent
Chen et al.

(10) Patent No.: US 11,179,617 B2
(45) Date of Patent: Nov. 23, 2021

(54) METHOD, VIRTUAL REALITY DEVICE, SYSTEM, AND NON-VOLATILE STORAGE MEDIA FOR PROVIDING VIRTUAL REALISTIC SCENES

(71) Applicant: Shanghai zhangmen science and Technology Co., Ltd., Shanghai (CN)

(72) Inventors: Danian Chen, Shanghai (CN); Xiaolin Tong, Shanghai (CN)

(73) Assignee: SHANGHAI ZHANGMEN SCIENCE AND TECHNOLOGY CO., LTD., Shanghai (CN)

( * ) Notice: Subject to any disclaimer, the term of this patent is extended or adjusted under 35 U.S.C. 154(b) by 75 days.

(21) Appl. No.: 15/678,129

(22) Filed: Aug. 16, 2017

(65) Prior Publication Data

US 2018/0050257 A1 Feb. 22, 2018

(30) Foreign Application Priority Data

Aug. 16, 2016 (CN) .......................... 201610673438.5
Aug. 16, 2016 (CN) .......................... 201610675279.2

(51) Int. Cl.
*A63B 22/02* (2006.01)
*A63B 24/00* (2006.01)
*A63B 22/00* (2006.01)
(Continued)

(52) U.S. Cl.
CPC ...... *A63B 71/0622* (2013.01); *A63B 22/0023* (2013.01); *A63B 22/025* (2015.10); *A63B 24/0062* (2013.01); *A63B 24/0087* (2013.01); *A63B 71/0054* (2013.01); *G16H 20/30* (2018.01); *A63B 2024/009* (2013.01);*A63B 2024/0096* (2013.01); *A63B 2071/0625* (2013.01); *A63B 2071/0636* (2013.01); *A63B 2071/0644* (2013.01);
(Continued)

(58) Field of Classification Search
CPC .............. A63B 71/0622; A63B 22/025; A63B 24/0087; A63B 71/0054; A63B 22/0023; A63B 24/0062; A63B 2024/009; A63B 2220/808; A63B 2071/0636; A63B 2024/0096; A63B 2071/0658; A63B 2220/803; A63B 2071/0625; A63B 2220/56; A63B 2071/0644; A63B 2220/807; A63B 2230/605; A63B 2220/836; A63B 2071/0666; A63B 71/0619; A63B 2071/0638; A63B 22/02; A63B 22/0235; A63B 22/0242; A63B 2022/0271; A63B 24/0084; G06T 11/00; G16H 20/30; H04N 13/282
See application file for complete search history.

(56) References Cited

U.S. PATENT DOCUMENTS 5,314,391 A * 5/1994 Potash ............... A63B 22/0023
340/573.1
5,431,612 A * 7/1995 Holden ................ A63B 21/157
482/54

(Continued)

*Primary Examiner* — Sundhara M Ganesan
*Assistant Examiner* — Shila Jalalzadeh Abyaneh
(74) *Attorney, Agent, or Firm* — Bayramoglu Law Offices LLC (57) ABSTRACT

The present invention relates to a method for providing virtual realistic scenes, a VR device, a system, and a nonvolatile storage medium. Virtual outdoor realistic sports scenes are generated via the VR device while a user is running motion on a treadmill apparatus. In addition, the virtual outdoor realistic sports scenes can be changed based on different motion states.

16 Claims, 5 Drawing Sheets

(51) Int. Cl.
  *A63B 71/06* (2006.01)
  *A63B 71/00* (2006.01)
  *G16H 20/30* (2018.01)
  *H04N 13/282* (2018.01)

(52) U.S. Cl.
  CPC ............ *A63B 2071/0658* (2013.01); *A63B 2071/0666* (2013.01); *A63B 2220/56* (2013.01); *A63B 2220/803* (2013.01); *A63B 2220/807* (2013.01); *A63B 2220/808* (2013.01); *A63B 2220/836* (2013.01); *A63B 2230/605* (2013.01); *H04N 13/282* (2018.05)

(56) References Cited

U.S. PATENT DOCUMENTS

| | | | | |
|---|---|---|---|---|
| 2006/0122035 A1* | 6/2006 | Felix | ............... | A63B 22/0023 482/8 |
| 2009/0111670 A1* | 4/2009 | Williams | ............... | G06F 3/011 482/146 |
| 2009/0186746 A1* | 7/2009 | Pandolfo | ............... | A61H 1/003 482/7 |
| 2010/0304931 A1* | 12/2010 | Stumpf | ............... | A63B 22/02 482/4 |
| 2011/0164044 A1* | 7/2011 | Huang | ............... | A63B 71/0622 345/473 |
| 2012/0040798 A1* | 2/2012 | Yu | ............... | A63B 22/0242 482/4 |
| 2014/0113770 A1* | 4/2014 | Yim | ............... | A63B 22/0023 482/8 |
| 2014/0274567 A1* | 9/2014 | McCready | ............... | G06F 3/011 482/8 |
| 2015/0011362 A1* | 1/2015 | Oh | ............... | A63B 71/0622 482/9 |
| 2016/0213976 A1* | 7/2016 | So | ............... | A63B 71/0622 |
| 2016/0317866 A1* | 11/2016 | Fung | ............... | A63F 13/212 |
| 2016/0361602 A1* | 12/2016 | Lagree | ............... | A63B 24/0087 |
| 2018/0224930 A1* | 8/2018 | Folmer | ............... | A63F 13/211 |

* cited by examiner

METHOD, VIRTUAL REALITY DEVICE, SYSTEM, AND NON-VOLATILE STORAGE MEDIA FOR PROVIDING VIRTUAL REALISTIC SCENES

CROSS REFERENCE TO RELATED APPLICATIONS

This application is based upon and claims priority to Chinese Patent Application No. 201610675279.2, filed on Aug. 16, 2016, and Chinese Patent Application No. 201610673438.5 filed on Aug. 16, 2016, the entire contents of which are incorporated herein by reference.

TECHNICAL FIELD

The present invention relates to the field of computers, and more particularly to a method, virtual reality device, system, and non-volatile storage media for providing virtual realistic scenes.

BACKGROUND

The sports environment of conventional treadmill, such as gym or bedroom, is usually tedious to users. In addition, the existing treadmill can only provide a two-dimensional movement.

SUMMARY

Based on an aspect of the present invention, a method for providing virtual outdoor realistic sports scenes using a system is provided. The method comprises generating the virtual outdoor realistic sports scenes via the VR device, while a user is running on the treadmill apparatus.

Based on another aspect of the present invention, a non-transitory computer readable medium storing a program causing a computer to execute a method for providing virtual outdoor realistic sports scenes is provided. The non-transitory computer readable medium comprises a module for generating a virtual outdoor realistic sports scene via a VR device, while a user is running on a treadmill apparatus.

Based on another aspect of the present invention, a system for providing virtual outdoor realistic sports scenes is provided. The system comprises a VR device configured to generate a virtual outdoor reality sports scene while the user is running on the treadmill apparatus.

BRIEF DESCRIPTION OF THE DRAWINGS

Other features, objectives, and advantages of the present invention will become more apparent from the detailed description of the non-limiting embodiments with reference to the following drawings.

The same or similar reference designators in the drawings represent the same or similar components.

DETAILED DESCRIPTION OF THE INVENTION

The invention will now be described in further detail with reference to the accompanying drawings.

in a typical configuration of the present invention, each of the terminal, the device and the trusted party of the service network includes one or more processors (CPU), input/output interfaces, network interfaces, and memory.

The memory may include the computer-readable media forms of non-permanent memory, random access memory (RAM), and/or nonvolatile memory such as read-only memory (R( )) or flash memory (flash RAM), etc. Memory is an example of a computer-readable medium.

The computer-readable medium including both permanent and non-permanent, and removable and non-removable media can be implemented to realize the information storage by any method or technology. The information can be computer readable instructions, data structure, program module, or other data. Examples of storage media of the computer include, but not limited to, phase change memory (PRAM), static random access memory (SRAM), dynamic random access memory (DRAM), other types of random access memory (RAM), read only memory (ROM), electrically erasable programmable read-only memory (EEPROM), flash memory or other memory technology, read-only optical disk read-only memory (CD-ROM), digital versatile disc (DVD)) or other optical storage, cassette magnetic tape, a magnetic tape/disk storage or other magnetic storage device or any other non-transmission medium, which can be used to store information that can be accessed by the computing device. As defined herein, the computer-readable medium does not include non-temporary computer-readable media (i.e. transitory media), such as modulated data signal and carrier.

Figure 1:
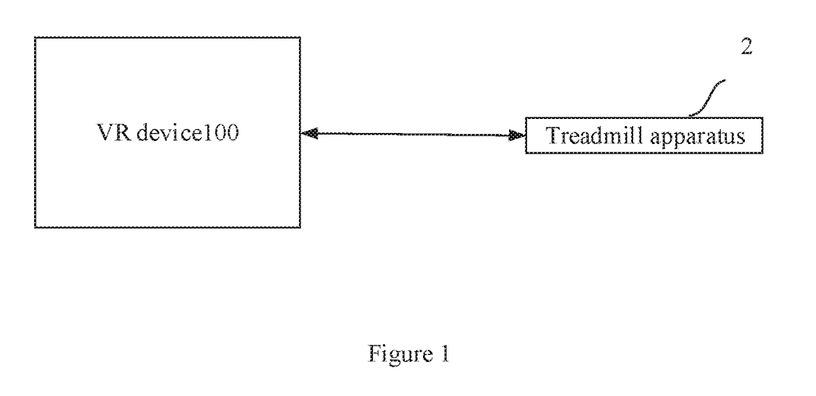
FIG. 1 shows a block diagram of a system for providing virtual realistic scenes based on one embodiment of the present invention.

As shown in FIG. 1, based on one aspect of the present invention, a system for providing virtual realistic scenes is provided. The system includes a VR (Virtual Reality) device 100. The VR device 100 includes any device that can be used to generate virtual scenes, such as a VR helmet, a pair of VR glasses, a projection screen, and the like. In some embodiments, the system further comprises treadmill apparatus 2.

VR device 100 generates virtual outdoor realistic sports scenes while the user is running on treadmill apparatus 2. Specifically, in the present embodiment, VR device 100 can work together with the treadmill apparatus to generate virtual outdoor realistic sports scenes while the user is running, so as to realize a sports environment with a specific virtual scenario including roads, buildings, and people of the sport. For example, the sports environment of running in the forest, road, park, river bank, mountains and the like can be generated. When the user is running, the corresponding buildings, trees, and people will move backward in a direction opposite to the running direction. As the movement of the user is accelerated, the backward speed of the buildings, trees, and people will increase accordingly. Based on the virtual realistic sports scenes, the user can complete the sport motion of running at a constant speed, running at an accelerated speed, turning, etc., such that the environmental experience for the user who is using the treadmill apparatus is enriched while the user is running, and a realistic sense of sport can be obtained.

In some embodiments of the present invention, VR device 100 also captures the motion state of the user while the user is running, and changes the virtual outdoor realistic sports scenes based on the motion state. Here, the virtual outdoor realistic sports scenes are changed based on different motion states. For example, when the user is running at a low speed, a virtual outdoor scene by the lake is provided. When the user is running at a high speed, a virtual outdoor scene of an arena track is provided. Thus, the match between the motion state and the specific virtual sports environment is achieved, such that the virtual outdoor realistic sports scene seen by the user is enriched. In some embodiments, VR device 100 acquires the m motion state of the user from treadmill apparatus 2 while the user is running, such as the running speed and the running mode of the user, etc. The running mode includes but not limited to the inclination angle and/or the inclination direction of the running platform or running track of treadmill apparatus 2 while the user is running.

Figure 2:
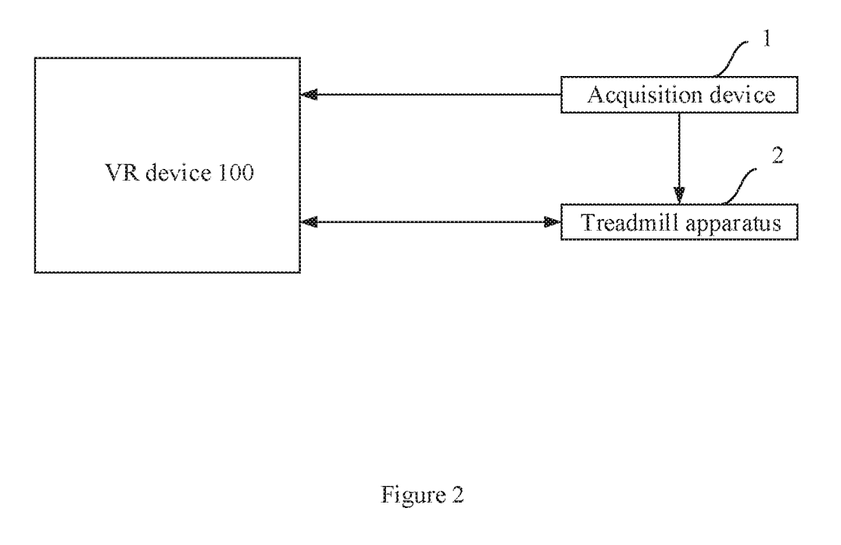
FIG. 2 shows a block diagram of a system for providing virtual realistic scenes based on another embodiment of the present invention.

In some embodiments, as shown in FIG. 2, the system for providing virtual realistic scenes further includes acquisition device 1, and VR device 100 which can acquire information from acquisition device 1 used for collecting the motion states. In some embodiments, acquisition device 1 includes, but not limited to, 3D (three dimensional) camera, three-axis gyroscope, and various sensors used for capturing the motion states of the user. Taking 3D camera as an example, generally, a plurality of 3D cameras can be provided and distributed around the user to shoot the user's motion postures in real-time. The motion postures are converted into a vector matrix of human physical spatial motion trend in real-time. The vector matrix coordinates may include human physical key feature point matrix, motion trend and speed associated with the feature point matrix, and displacement coordinates associated with the feature point matrix. The above vector matrix can represent the motion variation of the user when the motion is performed, so as to reflect the user's motion state. However, the three-axis gyroscope and various sensors can be directly worn on the user's body to detect the position variation of the user when the motion is performed, such that the corresponding data is obtained to determine the user's motion state. In some embodiments, the motion state acquired by VR device 100 is from treadmill apparatus 2 and acquisition device 1. In some embodiments, acquisition device 1 may also provide the acquired data to treadmill apparatus 2.

In some embodiments, the motion states include but not limited to one or any combination of a head rotation, a physical moving direction, a foot pressure distribution, an arm motion amplitude, a leg motion amplitude, and a muscle electrical signal of the user. For examples, when the user's head is moved from the left side to the right side, when the user's body turns to another direction, when the user's foot pressure distribution changes, when the user's arm motion amplitude changes, when the user's leg motion amplitude changes, or when the user's muscle electrical signal changes, different virtual outdoor scenes can be virtually switched by VR device 100 accordingly, so as to provide the user with richer and more realistic virtual scenes.

Figure 3:
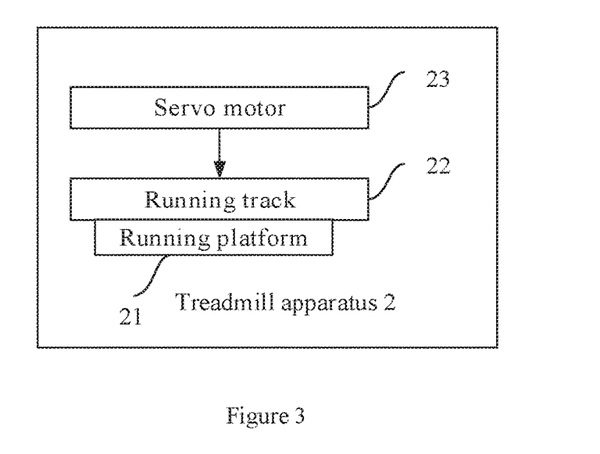
FIG. 3 shows a block diagram of a treadmill apparatus based on one embodiment of the present invention.

As shown in FIG. 3, in some embodiments, treadmill apparatus 2 includes running platform 21, running track 22 that is arranged on running platform 21, and motor 23 that drives running track 22. Specifically, the user may stand on running track 22 of running platform 21. Then, motor 23 drives running track 22 to achieve a basic function of straight running. Preferably, motor 23 includes a servo motor. In some embodiments, treadmill apparatus 2 is in communication with VR device 100 to provide the data of treadmill apparatus 2 to VR device 100. In some embodiments, the data includes but not limited to the user's running speed. In some embodiments, running platform 21 may be tilted. The data provided from treadmill apparatus 2 to VR device 100 may also include the inclination angle and/or the inclination direction of running platform 21 or running track 22.

Figure 4:
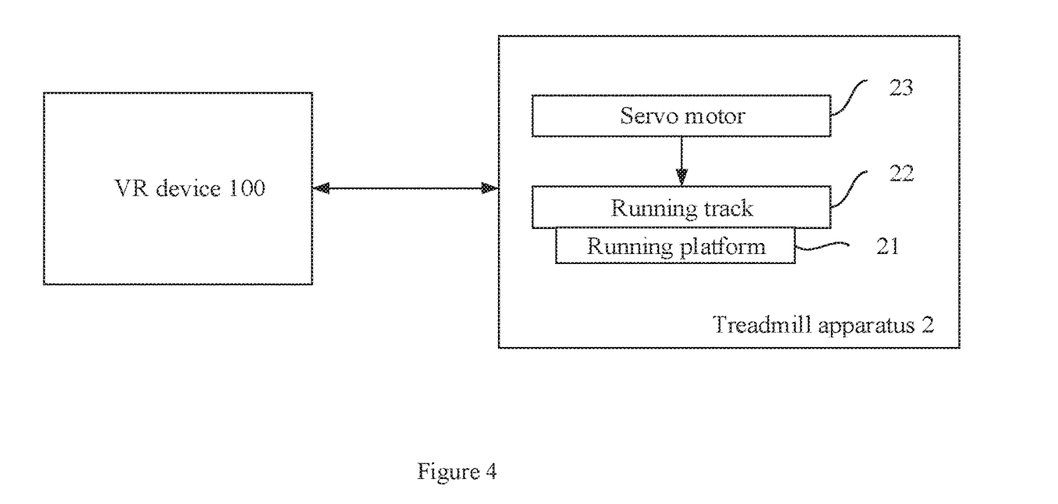
FIG. 4 shows a block diagram of a system for providing virtual realistic scenes based on still another embodiment of the present invention.

In some embodiments, as shown in FIG. 4, VR device 100 may send instructions to treadmill apparatus 2 to control the speed of running track 22 driven by motor 23 via treadmill apparatus 2, thereby adjusting the running speed of the user.

In some embodiments, VR device 100 may also send instructions to treadmill apparatus 2 based on one or any combination of the arm motion amplitude, the leg motion amplitude, and the muscle electrical signal of the user, so as to control the speed of running track 22 driven by motor 23. Thus, the running speed is automatically adjusted based on the user's motion state, the user's experience is enhanced. For example, when the user's arm motion amplitude is accelerated, when the leg motion amplitude is accelerated, or when the muscle electrical signal is stronger, motor 23 is controlled to accelerate the speed of running track 22.

Figure 5:
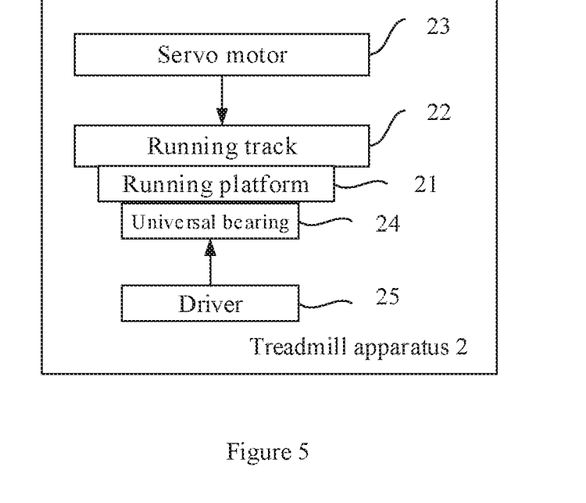
FIG. 5 shows a block diagram of a treadmill apparatus based on another embodiment of the present invention.
Figure 6:
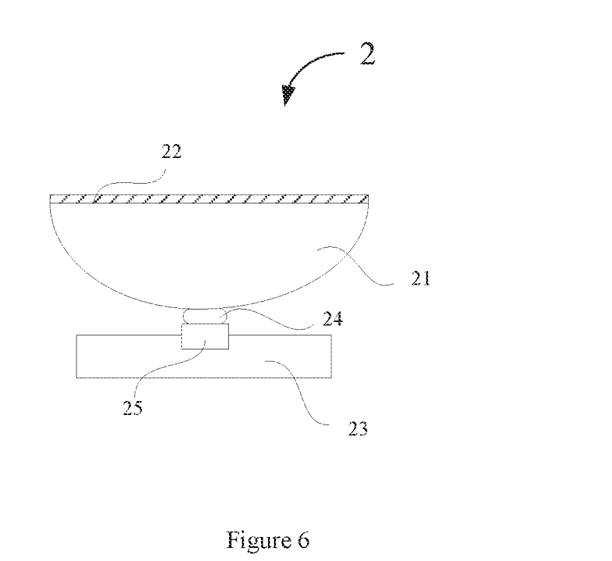
FIG. 6 shows a structural schematic diagram of a treadmill apparatus based on an embodiment of the present invention.

As shown in FIGS. 5 and 6, in some embodiments, treadmill apparatus 2 further includes universal bearing 24 arranged under running platform 21 and driver 25 driving universal bearing 24. The universal bearing is controlled to drive the running platform to incline at any angle, so as to change the inclination direction or height of the running platform. Thus, the functions of turning, uphill running, and downhill running can be realized for the user on the treadmill apparatus. The user's sports motion is more diverse. In some embodiments, the universal bearing 24 may be manually controlled to drive running platform 21 to change the inclination angle. Also, running platform 21 may be driven by instruction control to change the inclination angle. In some embodiments, the instructions for control may come from VR device 100 or treadmill apparatus 2. In some embodiments, VR device 100 issues instructions based on the data from treadmill apparatus 2 and/or acquisition device 1. In some embodiments, treadmill apparatus 2 issues instructions based on the data collected by itself and/or data from acquisition device 1. In some embodiments, driver 25 drives universal bearing 24 so as to drive running platform 21 to incline at a corresponding angle.

In some embodiments, VR device 100 generates the virtual outdoor realistic sports scenes of turning, uphill running, or downhill running while the user is running. That is, when the running platform changes the inclination direction or the height, the corresponding direction or height change is fed back to the virtual realistic sports scenes to change to a corresponding sport image, such that the user can experience the realistic scene of uphill running and downhill running while the user performs uphill running and downhill running on the treadmill apparatus. For example, a virtual outdoor scene of running uphill may be provided while the user performs the uphill running. Accordingly, a virtual outdoor scene of running downhill may be provided while the user performs the downhill running. Thus, the user can experience a vivid scenario during exercising.

In some embodiments, the VR device 100 or treadmill apparatus 2 may also control driver 25 to drive the universal bearing 24 based on one or any combination of the user's head rotation, physical moving direction, foot pressure distribution, muscle electrical signal, so as to drive running platform 22 to incline at a corresponding angle. Thus, the function of turning, uphill running, and downhill running of treadmill apparatus 2 can be automatically adjusted based on the user's motion state. For example, when the user's head turns, when the user's physical turns to another direction, when the user's foot pressure distribution changes, or when the user's muscle electrical signal changes, running platform 2 is controlled to adjust the inclination direction or height.

In some embodiments, VR device 100 may generate he virtual outdoor realistic sports scenes of the turning, uphill running, or downhill running while the user is running based on one or any combination of the user's head rotation, physical moving direction, foot pressure distribution, muscle electrical signal, running track speed, and running platform inclination angle. Thus, the virtual outdoor realistic sports scenes of the uphill and downhill running are automatically switched based on the user's motion state while the user is running uphill or downhill. As such, the user can have a more realistic experience of uphill and downhill running. In addition, an outdoor reality sports scene may be virtually generated based on the speed of the running track 22. For example, when the users are running at an accelerated speed, a decelerated speed, or a constant speed along a straight line on the running track 22, the virtual sports scene may change correspondingly. For instance, if the user is running forward at an accelerated speed, the scene will move backward at an accelerated speed. If the user is running forward at a decelerated speed, the scene will move backward at a decelerated speed. If the user is running forward at a constant speed, the scene will move backward at a constant speed.

In some embodiments, acquisition device 1 includes 3D image acquisition device 4 for collecting the user's physical image, and the user's physical image may be sent to VR device 100.

VR device 100 generates the virtual outdoor reality sports scene including the user's physical image while the user is running, so as to add the image of the user herself/himself to the virtual outdoor reality sports scene. Particularly, when there is a plurality of users running at the same time, a user can see the running figures of other users, such that sports scenes are enriched. Specifically, the 3D image acquisition device can be distributed around the treadmill apparatus, so as to accurately capture the user's physical motion images.

Figure 7:
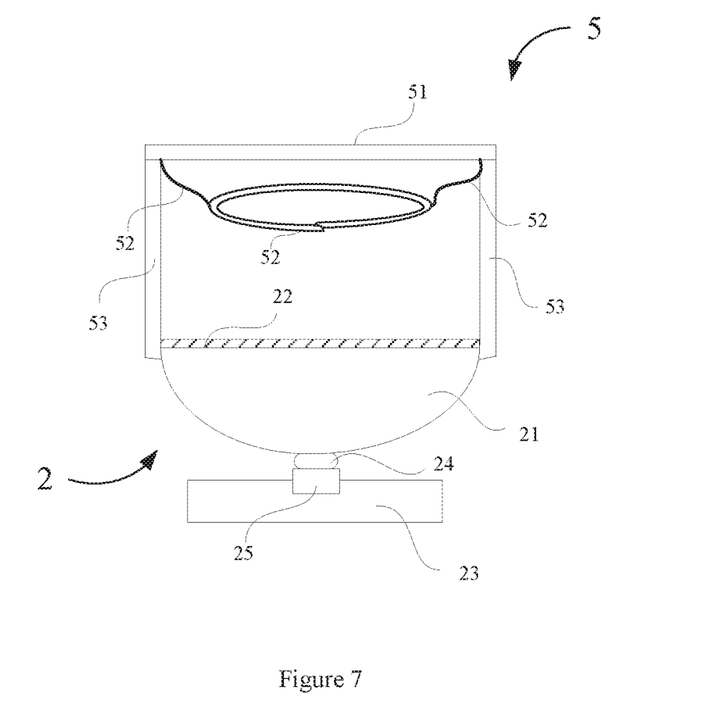
FIG. 7 shows a structural schematic diagram of a treadmill apparatus provided with a full guard based on an embodiment of the present invention.

Referring to FIG. 7, in some embodiments, treadmill apparatus 2 is provided with safety guard 5. The safety guard 5 includes:

fixing strut 53, wherein one end of the fixing strut is fixed to the treadmill apparatus, such as running platform 21;

guard frame 51, connected to the other end of fixing strut 53, wherein guard frame 51 may have any shape such as round, square, polygon, and the like; and the user can perform the running motion within the range defined by guard frame 51; and fixing belt 52, connected to guard frame 51, wherein fixing belt 52 can be fixed on the body of the user; and guard frame 51 and fixing belt 52 can prevent the user from falling down during the exercise.

VR device 100 may also acquire the voice from other user and play the voice. The voice of the other user may come from other system in communication with the system of VR device 100, so as to enable a language communication between users.

Figure 8:
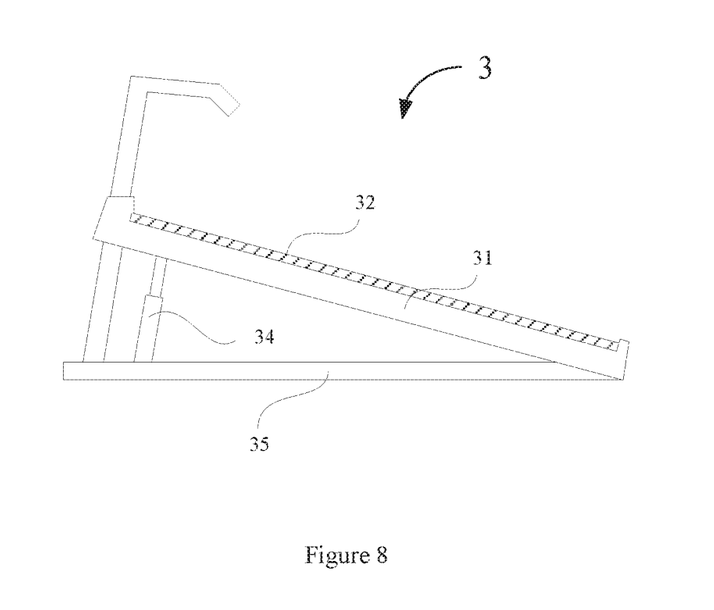
FIG. 8 shows a structural schematic diagram of a treadmill apparatus based on another embodiment of the present invention.

Referring to FIG. 8 which shows treadmill apparatus based on an embodiment of the present invention, treadmill apparatus 3 includes running platform 31 running track 32 provided on running platform 31, a motor (not shown) for driving the running track, lifting mechanism 34, and base 35. Lifting mechanism 34 is coupled to running platform 31. Lifting mechanism 34 can be controlled to stretch so as to control the inclination of running platform 31. In some embodiments, lifting mechanism 34 is manually controlled. In some embodiments, lifting mechanism 34 is controlled by instructions. The instructions may come from treadmill apparatus 3 or VR device 100. Treadmill apparatus 3 or VR device 100 may generate the instructions to control lifting mechanism 34 based on the data from treadmill apparatus 3 or acquisition device 1.

It should be noted that, FIG. 8 merely shows an embodiment where lifting mechanism 34 is provided at one end of running platform 31 to incline running platform 31 toward a specific direction. However, the present invention is not limited thereto. In fact, a plurality of lifting mechanisms 34 coupled to running platform 31 may be provided to control running platform 31 to be inclined toward a plurality of directions. For example, lifting mechanisms are provided on both ends of running platform 31 so that the running platform can be inclined toward two directions, so as to simulate the uphill and downhill running. For another example, lifting mechanisms may be provided at four corners of running platform 31 so that running platform 31 can be inclined toward a plurality of directions, etc.

It should be noted that, the above-mentioned treadmill apparatus 2 and treadmill apparatus 3 are merely examples to better illustrate the solution of the present invention. However, the treadmill apparatus of the present invention is not limited to the above-mentioned treadmill apparatus 2 and treadmill apparatus 3.

Figure 9:
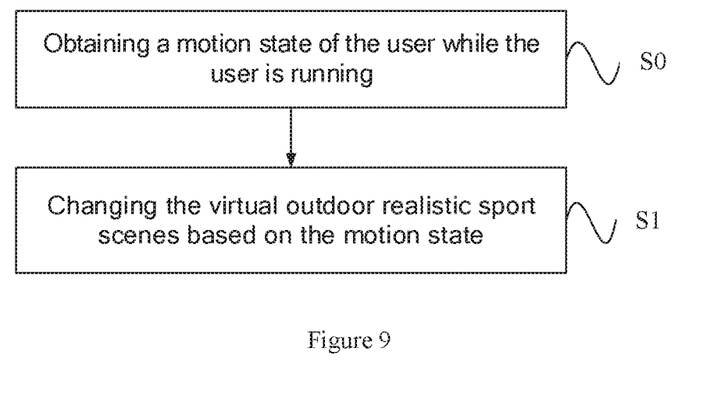
FIG. 9 shows a flow diagram of a method for providing virtual realistic scenes based on one embodiment of the present invention.

Based on an embodiment of the present invention, a method for providing virtual realistic scenes is provided, and the method includes:

Step S1, generating virtual outdoor realistic sports scenes via VR apparatus while a user is running on the treadmill apparatus. Specifically, the present embodiment can work together with the treadmill apparatus to generate virtual outdoor realistic sports scenes while the user is running, so as to realize a sports environment with a specific virtual scenario including roads, buildings, and people of the sport. For example, the sports environments of running in the forest, road, park, river bank, mountains, and the like can be generated. When the user is running, the corresponding buildings, trees, and people will move backward in a direction opposite to the running direction. As the movement of the user is accelerated, the backward speed of the buildings, trees, and people will increase accordingly. Based on the virtual realistic sports scenes, the user can complete the sport motion of running at a constant speed, running at an accelerated speed, turning, etc., such that the environmental experience for the user who is using the treadmill apparatus is enriched while the user is running, and a realistic sense of sport can be obtained.

In some embodiments, VR device 100 may receive a signal that indicates the state of the treadmill apparatus to determine whether the user is running on the treadmill apparatus. In some embodiments, the signal that indicates the state of the treadmill apparatus includes the signal that indicates the start or stop of the treadmill apparatus, the user's running speed, etc.

As shown in FIG. 8, in some embodiments, step SO is further included before step S1 to obtain the motion state of the user while the user is running. The step S1 includes changing a virtual outdoor reality sports scene based on the motion state. Here, the virtual outdoor realistic sports scenes are changed based on different motion states. For example, when the user is running at a low speed, a virtual outdoor scene by the lake is provided, When the user is running at a high speed, a virtual outdoor scene of arena track is provided. Thus, the match between the motion state and the specific virtual sports environment is achieved, such that the virtual outdoor realistic sports scenes seen by the user is enriched. In some embodiments, the signal that indicates the state of the treadmill apparatus may include at least a part of the motion state of the user while the user is running.

In some embodiments, the motion states include one or any combination of the user's head turning, physical moving direction, foot pressure distribution, arm motion amplitude, leg motion amplitude, and muscle electrical signal. Specifically, for examples, when the user's head is moved from the left side to the right side, when the user's body turns to another direction, when the user's foot pressure distribution changes, when the user's arm motion amplitude changes, when the user's leg motion amplitude changes or when the user's muscle electrical signal changes, different outdoor scenes may be virtually switched accordingly, so as to provide the user with richer and more realistic virtual scenes.

In some embodiments, the above-mentioned method for providing virtual realistic scenes further includes the following step, i.e., controlling the speed of the running track driven by the motor to adjust the running speed while the user is running on the treadmill apparatus.

In some embodiments, the above-mentioned method for providing virtual realistic scenes further includes the following step, i.e., controlling the speed of running track 22 driven by motor 23 based on one or any combination of the arm motion amplitude, the leg motion amplitude, and the muscle electrical signal of the user while the user is running on the treadmill apparatus. Thus, the running speed is automatically adjusted based on the user's motion state and the user's experience is enhanced. For example, when the user's arm motion amplitude is accelerated, when the leg motion amplitude is accelerated, or when the muscle electrical signal is stronger, the motor is controlled to accelerate the speed of running track. The motor can be controlled by the VR device or the treadmill apparatus to which the motor belongs, such that the speed of the running track can be adjusted.

In some embodiments, the treadmill apparatus further includes a universal bearing arranged under a running platform and a driver for driving the universal bearing. The universal bearing is controlled to drive the running platform to incline at any angle, so as to change the inclination direction or height of the running platform. Thus, the user can realize the functions of turning, uphill running, and downhill running on the treadmill apparatus. The diversity of the user's sports motion improved.

in some embodiments, the above-mentioned method for providing virtual realistic scenes further includes the following step, i.e., controlling the driver to drive the universal bearing when the user is running on the treadmill apparatus, so as to drive the running platform to incline at a corresponding angle. Thus, the inclination angle of the running platform of the treadmill apparatus is automatically adjusted, such that the function of uphill and downhill running can be realized for the user.

In some embodiments, the method of the above-mentioned step S1 for providing virtual realistic scenes includes the following step, i.e., generating the virtual outdoor realistic sports scenes of turning, uphill running, or downhill running while the user is running. That is, when the running platform changes the inclination direction or the height, the corresponding direction or height change is fed back to the virtual realistic sports scenes to change to a corresponding sport image, such that the user can experience the realistic scene of uphill running and downhill running while the user performs uphill running and downhill running on the treadmill apparatus. For example, a virtual outdoor scene of running uphill may be provided while the user performs the uphill running. Accordingly, a virtual outdoor scene of running downhill may be provided while the user performs the downhill running. Thus, the user can experience a vivid scenario during exercising.

In some embodiments, the above-mentioned method for providing virtual realistic scenes further includes the following step, i.e., controlling the driver to drive the universal bearing based on one or any combination of the user's head rotation, physical moving direction, foot pressure distribution, and muscle electrical signal while the user is running on the treadmill apparatus. As such, the running platform is driven to incline at a corresponding angle, such that the function of turning, uphill running, and downhill running of the treadmill apparatus can be automatically adjusted based on the user's motion state. For example, when the user's head turns, when the user's body turns to another direction, when the user's foot pressure distribution changes, or when the user's muscle electrical signal changes, the running platform is automatically adjusted to incline at a predetermined angle toward a certain direction.

In some embodiments, the step of the above-mentioned step S1 for providing virtual realistic scenes includes the following step, i.e., generating the virtual outdoor realistic sports scenes of the turning, uphill running, or downhill running based on one or any combination of the user's head rotation, the physical moving direction, the foot pressure distribution, the muscle electrical signal, and the running track speed while the user is running. Thus, the virtual outdoor realistic sports scenes are automatically switched to the uphill or downhill running based on the user's motion state while the user is running. As such, the user can experience a more realistic uphill and downhill running. In addition, an outdoor reality sports scene may be virtually generated based on the speed of the running track. For example, when the user is running at an accelerated speed, a decelerated speed, or a constant speed along a straight line on the running track, the virtual sports scene may change correspondingly. For instance, if the user is running forward at an accelerated speed, the scene will move backward at an accelerated speed. If the user is running forward at a decelerated speed, the scene will move backward at a decelerated speed. If the user is running forward at a constant speed, the scene will move backward at a constant speed.

In some embodiments, the step of the above-mentioned step S1 for providing virtual realistic scenes includes, i.e., generating the virtual outdoor realistic sports scenes of the turning, uphill running, or downhill running based on one or any combination of the user's head turning, the physical moving direction, the foot pressure distribution, the muscle electrical signal, and the inclination angle of the running platform while the user is running. Here, compared with the foregoing embodiment, a parameter of the inclination angle of the running platform is added in this embodiment, such that the virtual outdoor realistic sports scenes of the turning, uphill running, or downhill running generated while the user is running is more accurate.

In some embodiments, the above-mentioned method for providing virtual realistic scenes further includes the following step, i.e., collecting the user's physical image while the user is running. The step of the above-mentioned step S1 for providing virtual realistic scenes includes the following step, i.e., generating the virtual outdoor reality sports scene including the physical image of the user while the user is running. Therefore, the figure of the user himself/herself is added to the virtual outdoor reality sports scene. Particularly, when there is a plurality of users running at the same time, a user can see the running figures of other users, such that the sports scenes are enriched. Specifically, the function of collecting the user's physical image can be completed by the acquisition device. The acquisition device can be distributed around the treadmill apparatus, so as to accurately capture the user's physical motion images.

To conclude, in the present invention, the virtual outdoor reality sports scene is generated while the user is running on the treadmill apparatus. The virtual outdoor reality sports scene can work together with the treadmill apparatus to generate the virtual outdoor reality sports scene while the user is running, so as to realize the sports environment under the specific virtual scenario. Thus, while the user is running, the environmental experience of the user of the treadmill apparatus is enriched, such that a realistic sense of sport can he achieved. In addition, by changing the virtual outdoor reality sports scene based on different motion states, the motion posture and the specific virtual sports environment are matched with each other, such that the virtual outdoor reality sports scene seen by the is more diverse.

Apparently, without departing from the spirit and scope of the present invention, those skilled in the art can make various modifications and variations to the present invention. In this manner, if the modifications and variations of the present invention fall within the scope of the appended claims and the equivalents thereof, the present invention is intended to include these modifications and variations.

It should be noted that the present invention may be implemented in software and/or the combination of software and hardware, for example, the present invention can be implemented by means of application specific integrated circuit (ASIC), general purpose computer, or any other similar hardware device. In one embodiment, the software program of the present invention may be executed by a processor to realize the steps or functions described above. Similarly, the software program (including the associated data structure) of the present invention may be stored in a computer readable recording medium, such as a RAM memory, a magnetic or optical driver, or a floppy disk and the like. In addition, some of the steps or functions of the present invention may be implemented by means of hardware, for example, the circuit in combination with the processor to perform each step or function.

In addition, the present invention may be partially applied as a computer program product, such as computer program instructions. For example, when the computer program instructions are implemented by a computer, the method and/or technical solution of the present invention may be invoked or provided based on the operation of the computer. Moreover, the program instructions that invoke the method of the present invention may be stored in a fixed or removable recording medium, and/or transmitted through broadcasting or the data stream in other signal-carrying medium, and/or stored in a work storage of the computer device operated based on the program instructions. Here, an apparatus is provided based on one embodiment of the present invention, the apparatus includes a memory configured to store the computer program instructions and a processor configured to execute the program instructions. When the computer program instructions are executed by the processor, the apparatus is triggered to operate the method and/or technical solution based on various foregoing embodiments of the present invention.

It will be apparent to those skilled in the art that the present invention is not limited to the details of the above-mentioned exemplary embodiments. Without departing from the spirit or essential features, the present invention may be practiced in other specific forms. Accordingly, the embodiments should be exemplarily considered in any aspect and are non-restrictive. The scope of the invention is defined by the appended claims rather than the foregoing description. Therefore, the present invention is intended to include all variations of the meaning and scope of the equivalent elements falling within the scope of the present invention. The reference designators in the claims should not be construed as limitations of the claims. In addition, it is clear that the term "include" does not exclude other units or steps, and the singular does not exclude the plural. The plurality of elements or devices described in the device claims may also be implemented by software or hardware via one unit or device. The terms of first, second and other words are used to express the name rather than indicating any specific order.

What is claimed is:

1. A system providing virtual outdoor realistic sports scenes, comprising:
   a virtual reality (VR) device capturing a motion state of a user while the user is running on a treadmill apparatus and automatically switching to different virtual outdoor realistic sports scenes based on different motion states of the user, wherein the treadmill apparatus comprises:
   a driver configured to drive a universal bearing based on one or any combination of a user's head rotation, physical moving direction, foot pressure distribution or muscle electrical signal to drive a running platform to incline at an angle, wherein the universal bearing is arranged under the running platform;
   an acquisition device collecting a physical image of the user while the user is running on the treadmill apparatus, wherein the virtual outdoor realistic sports scenes include the physical image of the user;
   wherein the treadmill apparatus further comprises a motor and controls a speed of a running track driven by the motor based on an arm motion amplitude while the user is running on the treadmill apparatus.

2. The system of claim 1, further comprising the treadmill apparatus wherein the running track is arranged on the running platform.

3. The system of claim 2, wherein the motor is a servo motor.

4. The system of claim 1, wherein the acquisition device further collects the motion state of the user.

5. The system of claim 1, further comprising:
a safety guard, configured to protect the user from falling down while the user is running on the treadmill apparatus.

6. The system of claim 1, wherein the VR device is a helmet or glasses.

7. The system of claim 2, wherein the acquisition device comprises a three-axis gyroscope and a 3D camera.

8. A non-transitory computer readable medium storing a program causing a computer to execute a method of providing virtual outdoor realistic sports scenes, comprising:
a module generating the virtual outdoor realistic sports scenes via a virtual reality (VR) device, the VR device captures a motion state of a user while the user is running on a treadmill apparatus and automatically switches to different virtual outdoor realistic sports scenes based on different motion states of the user, and
a module collecting a physical image of the user while the user is running on the treadmill apparatus, wherein the virtual outdoor reality sports scenes include the physical image of the user;
wherein the treadmill apparatus comprises: a driver configured to drive a universal bearing based on one or any combination of a user's head rotation, physical moving direction, foot pressure distribution or muscle electrical signal to drive a running platform to incline at an angle, wherein the universal bearing is arranged under the running platform;
wherein the treadmill apparatus further comprises a motor and controls a speed of a running track driven by the motor based on an arm motion amplitude while the user is running on the treadmill apparatus.

9. The non-transitory computer readable medium of claim 8, further comprising:
a module obtaining the motion state of the user via an acquisition device while the user is running.

10. A method of providing virtual outdoor realistic sports scenes, comprising:
providing a treadmill apparatus comprising:
a running platform,
a universal bearing arranged under the running platform,
a motor driving a running track, and
a driver configured to drive the universal bearing,
providing a system including a virtual reality (VR) device;
capturing, by the VR device, a motion state of a user while the user is running on the treadmill apparatus;
collecting a physical image of the user while the user is running on the treadmill apparatus, wherein the virtual outdoor reality sports scenes include the physical image of the user;
driving, by the driver, the universal bearing to drive the running platform to incline at an angle based on the motion state of the user;
automatically switching to different virtual outdoor realistic sports scenes based on different motion states of the user; and
controlling a speed of the running track driven by the motor based on an arm motion amplitude while the user is running on the treadmill apparatus.

11. The method of claim 10, further comprising: obtaining the motion state of the user via an acquisition device while the user is running.

12. The method of claim 11, wherein the motion state is selected from the group consisting of a head turning, a physical moving direction, a foot pressure distribution, the arm motion amplitude, a leg motion amplitude, a muscle electrical signal of the user, and any combination thereof.

13. The method of claim 10,
wherein the running track is arranged on the running platform.

14. The method of claim 10, wherein the driver is controlled based on one or any combination selected from the group consisting of a head rotation, a physical moving direction, a foot pressure distribution, and a muscle electrical signal of the user while the user is running on the treadmill apparatus.

15. The method of claim 10, wherein the virtual outdoor realistic sports scene is selected from the group consisting of an uphill running, and a downhill running.

16. The method of claim 10, further comprising: collecting a voice of the user or playing a collected voice of the user.

* * * * *